United States Patent
Von Strempel

(10) Patent No.: US 6,179,875 B1
(45) Date of Patent: Jan. 30, 2001

(54) IMPLANT FOR FUSING LUMBAR VERTEBRAE AND METHOD OF USING SAME

(75) Inventor: Archibald Von Strempel, Burgwedel/Thönse (DE)

(73) Assignee: Ulrich GmbH & Co. KG, Ulm (DE)

( * ) Notice: Under 35 U.S.C. 154(b), the term of this patent shall be extended for 0 days.

(21) Appl. No.: 09/334,791

(22) Filed: Jun. 16, 1999

(30) Foreign Application Priority Data

Jun. 17, 1998 (DE) .............................................. 198 26 619

(51) Int. Cl.[7] ....................................................... A61F 2/44
(52) U.S. Cl. ...................................... 623/17.16; 623/17.11
(58) Field of Search ............................ 623/17.11, 17.16, 623/16.11, 17; 606/61

(56) References Cited

U.S. PATENT DOCUMENTS

| | | | |
|---|---|---|---|
| 4,834,757 | * | 5/1989 | Brantigan ........................... 623/17.11 |
| 4,904,261 | * | 2/1990 | Dove et al. ......................... 623/17.16 |
| 5,192,327 | * | 3/1993 | Brantigan ........................... 623/17.11 |
| 5,397,364 | * | 3/1995 | Kozak et al. ....................... 623/17.11 |
| 5,522,899 | * | 6/1996 | Michelson ...................... 623/17.16 X |
| 5,609,635 | * | 3/1997 | Michelson ......................... 623/17.16 |
| 5,716,415 | * | 2/1998 | Steffee ............................... 623/17.16 |
| 5,766,252 | * | 6/1998 | Henry et al. ....................... 623/17.16 |
| 5,776,199 | * | 7/1998 | Michelson ......................... 623/17.16 |
| 5,888,227 | * | 3/1999 | Cottle ................................. 623/17.16 |

\* cited by examiner

Primary Examiner—Jeffrey A. Smith
(74) Attorney, Agent, or Firm—Herbert Dubno; Andrew Wilford

(57) ABSTRACT

An implant for intersomatic fusion of two adjacent vertebrae has a web plate and a pair of arms extending from ends of the web plate and imparting a U-shape to the implant. The arms forming with the web plate a space. Such implants are used to stabilize two adjacent vertebrae following resection of a disk between them and distraction of the two vertebrae to form between confronting faces of the vertebrae a gap through which the patient's spinal chord extends. The implants are inserted into the gap from the posterior to each side of the spinal chord and then the spaces defined between the arms are packed with bone chips. Such a procedure is, by comparison with the standard anterior approach, relatively noninvasive and therefore is much less expensive and difficult for the patient.

14 Claims, 4 Drawing Sheets

IMPLANT FOR FUSING LUMBAR VERTEBRAE AND METHOD OF USING SAME

FIELD OF THE INVENTION

The present invention relates to the fusing of spinal vertebrae. More particularly this invention concerns an implant for fusing lumbar vertebra and a method of using the implant.

BACKGROUND OF THE INVENTION

When a defective disk has been removed from between two vertebrae it is necessary to provide an implant to maintain a spacing between these vertebrae so that the spine is not unstable in the region of the resected disk and to prevent the two bones from rubbing painfully together. As a rule such implants are generally closed cages whose interiors are only accessible through small apertures in their side walls. Bone chips must be introduced into the interior of such an implant so the two flanking vertebrae will grow and fuse together. This is a fairly difficult job, and necessitates the use of tiny bone fragments that do not grow well and that are quite hard to handle. Furthermore the job of packing the implant can take quite some time due to the smallness of the bone fragments, making the operation fairly long and, hence, even more expensive and dangerous for the patient than is strictly necessary.

OBJECTS OF THE INVENTION

It is therefore an object of the present invention to provide an improved implant for fusing two vertebrae.

Another object is the provision of such an improved implant for fusing two vertebrae which overcomes the above-given disadvantages, that is which is easy to install and which promotes rapid bone growth and fusion.

A further object is the provision of an improved method of stabilizing vertebrae by means of an implant for a spinal fusion.

SUMMARY OF THE INVENTION

An implant for intersomatic fusion of two adjacent vertebrae has according to the invention a web plate and a pair of arms extending from ends of the web plate and imparting a U-shape to the implant. The arms form with the web plate a space.

Such implants are used to stabilize two adjacent vertebrae following resection of a disk between them and distraction of the two vertebrae to form between confronting faces of the vertebrae a gap through which the patient's spinal chord extends. The implants are inserted into the gap from the posterior to each side of the spinal chord and then the spaces defined between the arms are packed with bone chips. Such a procedure is, by comparison with the standard anterior approach, relatively noninvasive and therefore is much less expensive and difficult for the patient.

According to the invention one of the arms of each implant extends substantially at a right angle to the respective web plate and the other of the respective arms extends at an acute angle to the respective web plate and to the respective one arm. The two implants are positioned with their one arms immediately adjacent and generally parallel to each other. Thus the two angled-out arms are on the outside, with the planes of the web plate and arms perpendicular to the faces of the flanking vertebrae for very solid engagement.

The web plate in accordance with the invention is formed with a tool-receiving hole and the implants are inserted by being mounted at the hole onto a tool and pushed by the tool into the space. The hole is threaded and the tool has a threaded end.

The bone chips according to the invention are obtained autologously from the patient, typically from the pelvis. Normally in accordance with the invention the arms have free ends formed with inwardly directed holding formations and the chips include a bone plate fixed crosswise between the arms at the formations. The arms are formed with throughgoing holes so that bone can grow through the holes. More bone chips are normally packed around the implant, to fuse through the holes with the chips in the spaces.

The edges of the arms according to the invention are formed with angled barbs that are directed away from the web plate. Thus they can be pushed into place, but will lock there and not move once whatever is used to distract the vertebrae is released.

BRIEF DESCRIPTION OF THE DRAWING

The above and other objects, features, and advantages will become more readily apparent from the following description, reference being made to the accompanying drawing in which.

SPECIFIC DESCRIPTION

Figure 6:
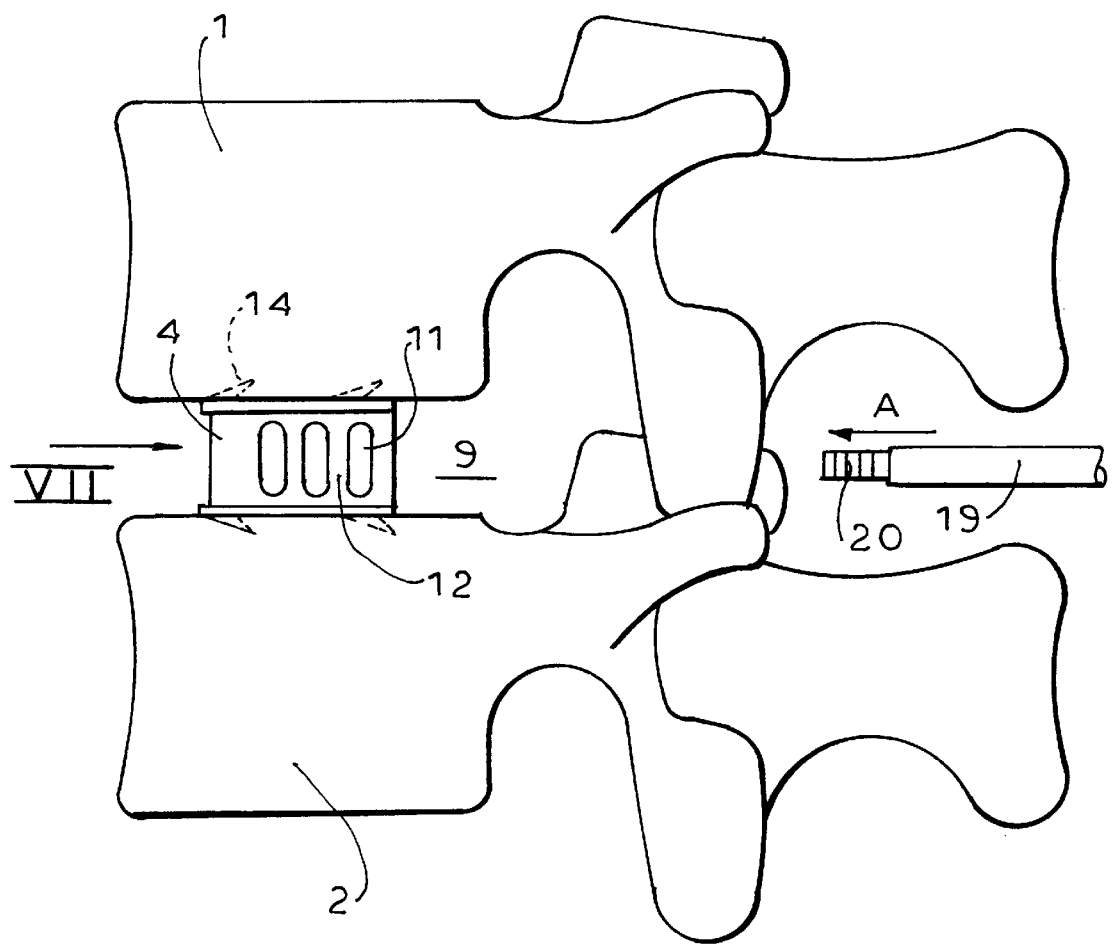
FIG. 6 is a side view showing the implant installed between two lumbar vertebrae.
Figure 7:
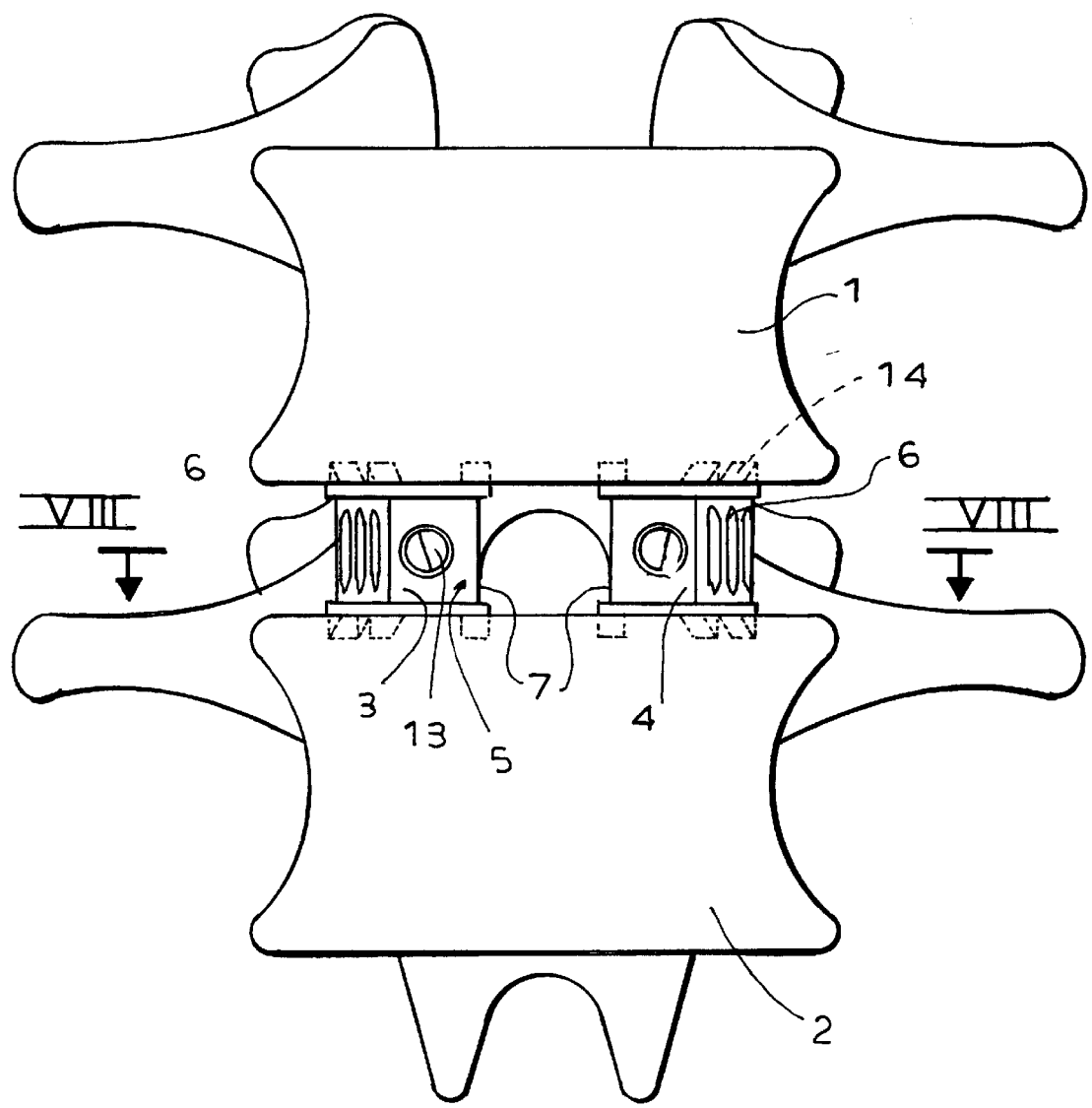
FIG. 7 is a view taken in the direction of arrow VII of FIG. 6.
Figure 8:
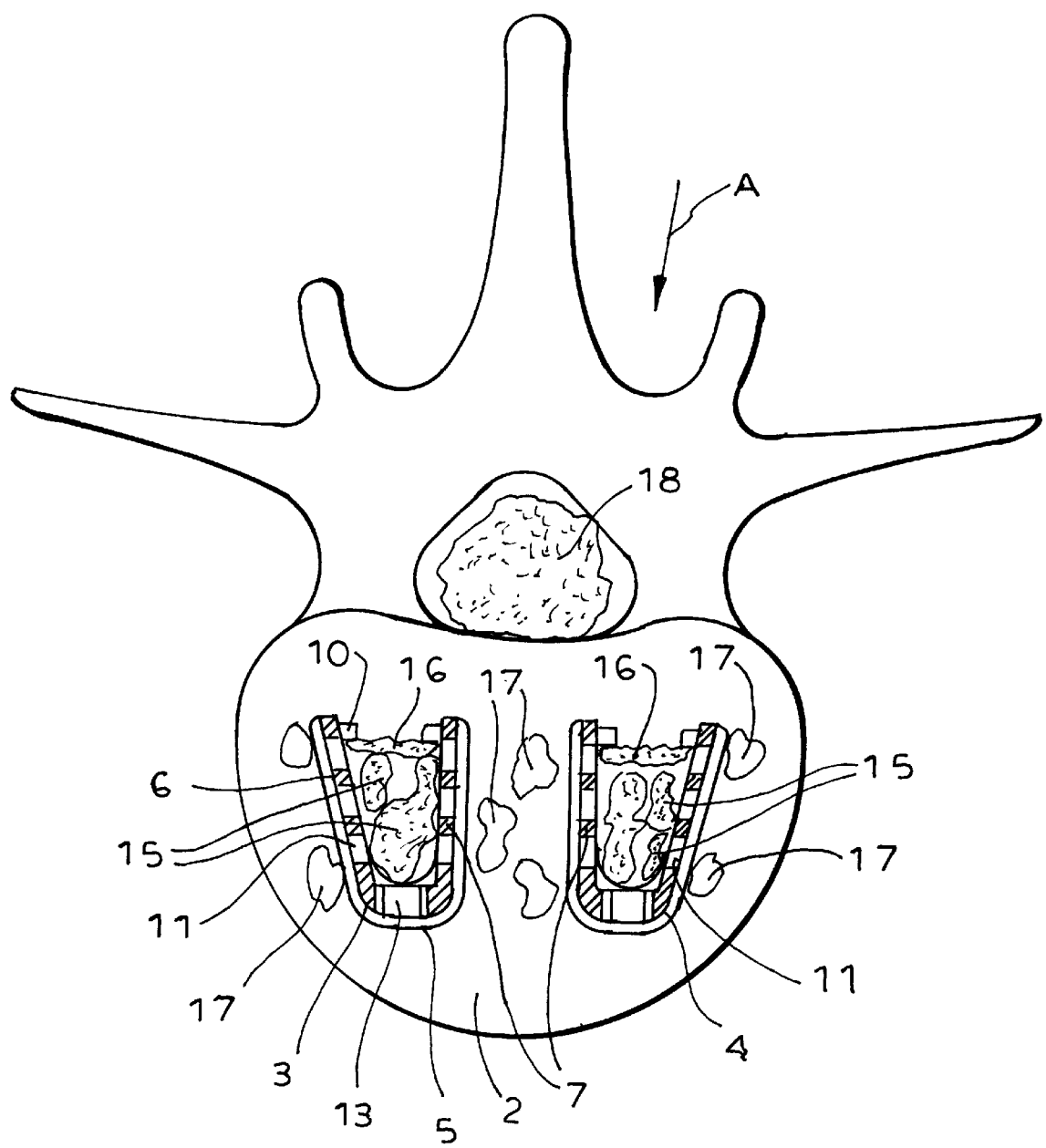
FIG. 8 is a section taken along line VIII—VIII of FIG. 7.

A pair of lumbar vertebrae 1 and 2 shown in FIGS. 6, 7, and 8 are separated and stabilized so they can fuse together by means of implants 3 and 4 shown in FIGS. 1 through 5. The implants 3 and 4 are identical or mirror symmetrical to each other.

Figure 1:
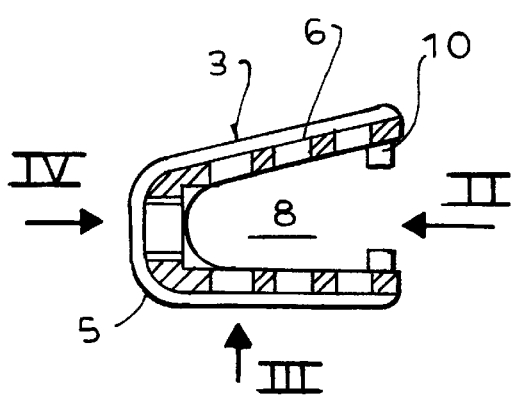
FIG. 1 is a horizontal section through an implant according to the invention.
Figure 2:
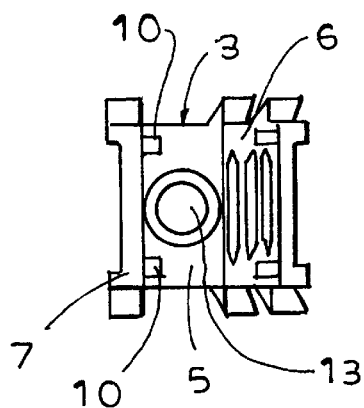
FIGS. 2, 3, and 4 are views taken in the directions of arrows II, III, and IV of FIG. 1.
Figure 3:
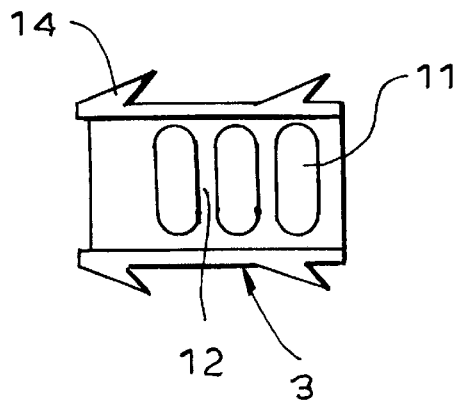
Figure 4:
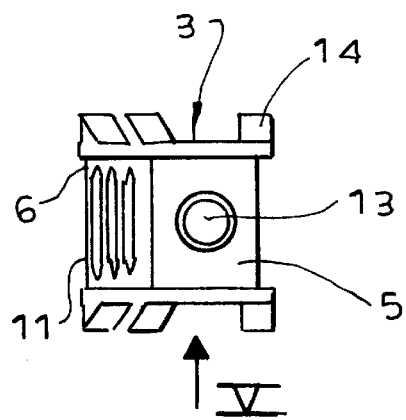
Figure 5:
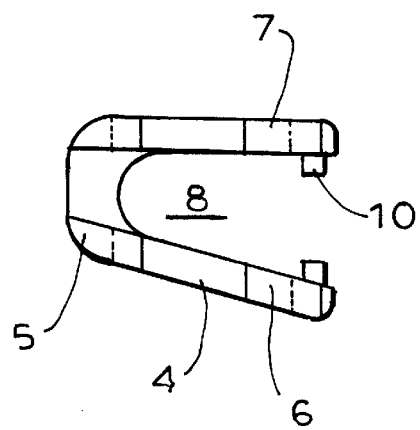
FIG. 5 is a view taken m the direction of arrow V of FIG. 4.

Each implant 3 shown in detail in FIGS. 1 to 4 is basically U-shaped and made of steel. It has a web 5 from which project a pair of arms 6 and 7, the latter extending at a right angle to the web 5 and the former at an acute angle to the arm 7 as best seen in FIG. 1. The two arms 6 and 7 define a fairly large space 8 adapted to be filled with bone chips 15 (FIG. 8) that will grow together with the vertebrae 1 and 2 when the two implants 3 and 4 are set in a gap 9 between these vertebrae 1 and 2.

The arms 6 and 7 are formed at their outer ends with inwardly directed holding formations 10 constituted as small pins that serve to retain chunks or plates 16 (FIG. 8) of bone in the space 8. In addition each arm 6 and 7 is formed with through-going slots 11 separated by webs 12 so that bone and tissue growth through these arms 6 and 7 is insured, while they still are relatively crush proof since the webs 12 are continuous in the vertical loading direction.

A threaded hole 13 is formed in the web 5 that serves for installing the implant 3 or 4, and that serves after installation for throughgrowth of bone and tissue. In addition the edges of the arms 6 and 7 are formed with barbs 14 that bite into and secure the implants 3 and 4 solidly in place in the gap 9.

As shown in FIGS. 6 to 8, after resection of a disk from between the two vertebrae 1 and 2 these vertebrae 1 and 2 are wedged or otherwise distracted to maintain or form the gap 9 between them. The two implants 3 and 4 are then inserted in place by screwing a threaded end 20 of an insertion tool or rod 19 into the respective hole 13 and pushing them into place to opposite sides of the spinal column, working from the posterior as indicated by arrow A so that the barbs 14 do not catch on the bodies of the vertebrae 1 and 2. As clearly visible in FIG. 8 the two implants 3 and 4 are inserted with their right-angle legs 7 toward and parallel to each other and their angled-out legs 6 on the outside for broadest possible support of the two vertebrae 1 and 2 against each other.

Once in place the insertion tools 19 are unscrewed from the holes 13 and removed, and any devices maintaining the distraction of the vertebrae 1 and 2 are released so that the vertebrae 1 and 2 settle solidly on the two implants 1 and 2. Then the spaces 8 are packed with bone chips 15 which can be taken from the pelvis of the patient. Due to the large size of the spaces 8, it is possible to use large pieces that will quickly fuse to the adjacent vertebrae 1 and 2. A flat bone plate 16 also obtained autologously from the patient is caught on the holding pins 10 to retain the chips 15 in place.

The result is a solid relative positioning of the two vertebrae 1 and 2 in an operation that can be done entirely from the posterior. The two implants 3 and 4 can easily be fitted in place, working from respective sides of the delicate spinal chord 18, and can be filled with relatively large chunks of bone, including the bone plate 16 caught on the holder pins 10, to hold everything in the space 8 in position. More bone chips 17 are then packed around the outsides of the implants 3 and 4 so that bone grows through the holes 11. Since all of the spaces 8 are open toward the respective upper and lower faces of the flanking vertebrae 1 and 2, good fusion is ensured.

I claim:

1. An implant for intersomatic fusion of two adjacent vertebrae, the implant comprising:
    a web plate; and
    a pair of arms extending from ends of the web plate and imparting a U-shape to the implant, the arms forming with the web plate a space, one of the arms extending substantially at a right angle to the web plate and the other of the arms extending at an acute angle to the one arm.

2. The implant defined in claim 1 wherein the arms have free ends formed with inwardly directed holding formations.

3. The implant defined in claim 2 wherein the holding formations are pins.

4. The implant defined in claim 1 wherein the arms are formed with throughgoing holes, whereby bone can grow through the holes.

5. The implant defined in claim 4 wherein the holes are separated by continuous transverse webs.

6. The implant defined in claim 1 wherein the web plate is formed with a tool hole.

7. The implant defined in claim 1 wherein edges of the arms are formed with angled barbs.

8. The implant defined in claim 7 wherein the barbs are directed away from the web plate.

9. A method of stabilizing two adjacent vertebrae following resection of a disk between them and distraction of the two vertebrae to form between confronting faces of the vertebrae a gap through which the patient's spinal chord extends, the method comprising the steps of:
    inserting into the gap from the posterior to each side of the spinal chord a respective U-shaped implant having a flat web plate and a pair of flat arms extending from ends of the web plate and forming with the web plate a space open both posteriorly and toward the faces of the vertebrae; and
    packing the spaces with bone chips.

10. The method defined in claim 9 wherein one of the arms of each implant extends substantially at a right angle to the respective web plate and the other of the respective arms extends at an acute angle to the respective one arm, the method comprising the step of positioning the two implants with their one arms immediately adjacent and generally parallel to each other.

11. The method defined in claim 9 wherein the web plate is formed with a tool-receiving hole, the implants being inserted by being mounted at the hole onto a tool and pushed by the tool into the space.

12. The method defined in claim 11 wherein the hole is threaded and the tool has a threaded end.

13. The method defined in claim 9 wherein the bone chips are obtained autologously from the patient.

14. The method defined in claim 13 wherein the arms have free ends formed with inwardly directed holding formations, the chips including a bone plate fixed crosswise between the arms at the formations.

* * * * *